(12) United States Patent
Sann et al.

(10) Patent No.: US 7,343,925 B2
(45) Date of Patent: Mar. 18, 2008

(54) DEVICE AND METHOD FOR EXTRACTING LIQUID SAMPLES

(75) Inventors: Heiner Sann, Magdeburg (DE); Andreas Bock, Magdeburg (DE); Udo Reichl, Burgwedel (DE)

(73) Assignee: Max-Planck-Gesellschaft Zur, Munich (DE)

( * ) Notice: Subject to any disclaimer, the term of this patent is extended or adjusted under 35 U.S.C. 154(b) by 220 days.

(21) Appl. No.: 10/530,156

(22) PCT Filed: Oct. 1, 2003

(86) PCT No.: PCT/EP03/10883

§ 371 (c)(1),
(2), (4) Date: Jul. 18, 2005

(87) PCT Pub. No.: WO2004/033077

PCT Pub. Date: Apr. 22, 2004

(65) Prior Publication Data

US 2006/0027264 A1     Feb. 9, 2006

(30) Foreign Application Priority Data

Oct. 2, 2002 (DE) ............................ 102 46 262

(51) Int. Cl.
B67D 5/54 (2006.01)
(52) U.S. Cl. ............................ 137/212; 137/240
(58) Field of Classification Search ............ 141/85–92, 141/8, 65; 137/212, 238, 240
See application file for complete search history.

(56) References Cited

U.S. PATENT DOCUMENTS

| | | | |
|---|---|---|---|
| 3,428,413 A | * | 2/1969 | Froelich .................. 422/111 |
| 4,501,161 A | | 2/1985 | Endo et al. ............... 73/863.24 |
| 5,316,181 A | * | 5/1994 | Burch ...................... 222/61 |
| 5,636,763 A | * | 6/1997 | Furness ..................... 222/54 |
| 5,857,590 A | * | 1/1999 | Kao et al. .................. 222/1 |
| 5,948,998 A | | 9/1999 | Witte et al. ............... 73/864.14 |
| 6,460,730 B1 | * | 10/2002 | Liedtke ...................... 222/1 |

FOREIGN PATENT DOCUMENTS

| | | |
|---|---|---|
| DE | 32 49 399 | 3/1984 |
| DE | 44 07 439 | 1/1995 |
| DE | 195 30 886 | 10/1996 |
| DE | 297 05 206 | 7/1997 |
| EP | 0 165 801 | 12/1985 |
| EP | 357 998 | 3/1990 |
| EP | 1 116 509 | 7/2001 |
| FR | 2 617 286 | 12/1988 |
| FR | 2 647 213 | 11/1990 |
| JP | 60 219539 | 11/1985 |
| JP | 06 098758 | 4/1994 |
| WO | WO 99/40175 | 8/1999 |

* cited by examiner

Primary Examiner—Ramesh Kirshnamurthy
Assistant Examiner—Craig Schneider
(74) Attorney, Agent, or Firm—Needle & Rosenberg, P.C.

(57) ABSTRACT

The invention relates to a device and a method for extracting liquid samples from containers (1) and/or tubes filled with a medium (2), especially from fermenters, via a filter membrane (5) by means of a partial vacuum. Said filter membrane (5) arranged inside a sample probe (3) consists of a material acting as a sterile boundary, a supply line (6) which can be used to guide gas and a discharge line (7) which can be used to guide the sample being arranged on the sterile boundary side (5a) of the filter membrane (5).

21 Claims, 3 Drawing Sheets

DEVICE AND METHOD FOR EXTRACTING LIQUID SAMPLES

CROSS REFERENCE TO RELATED APPLICATION

Figure 1:
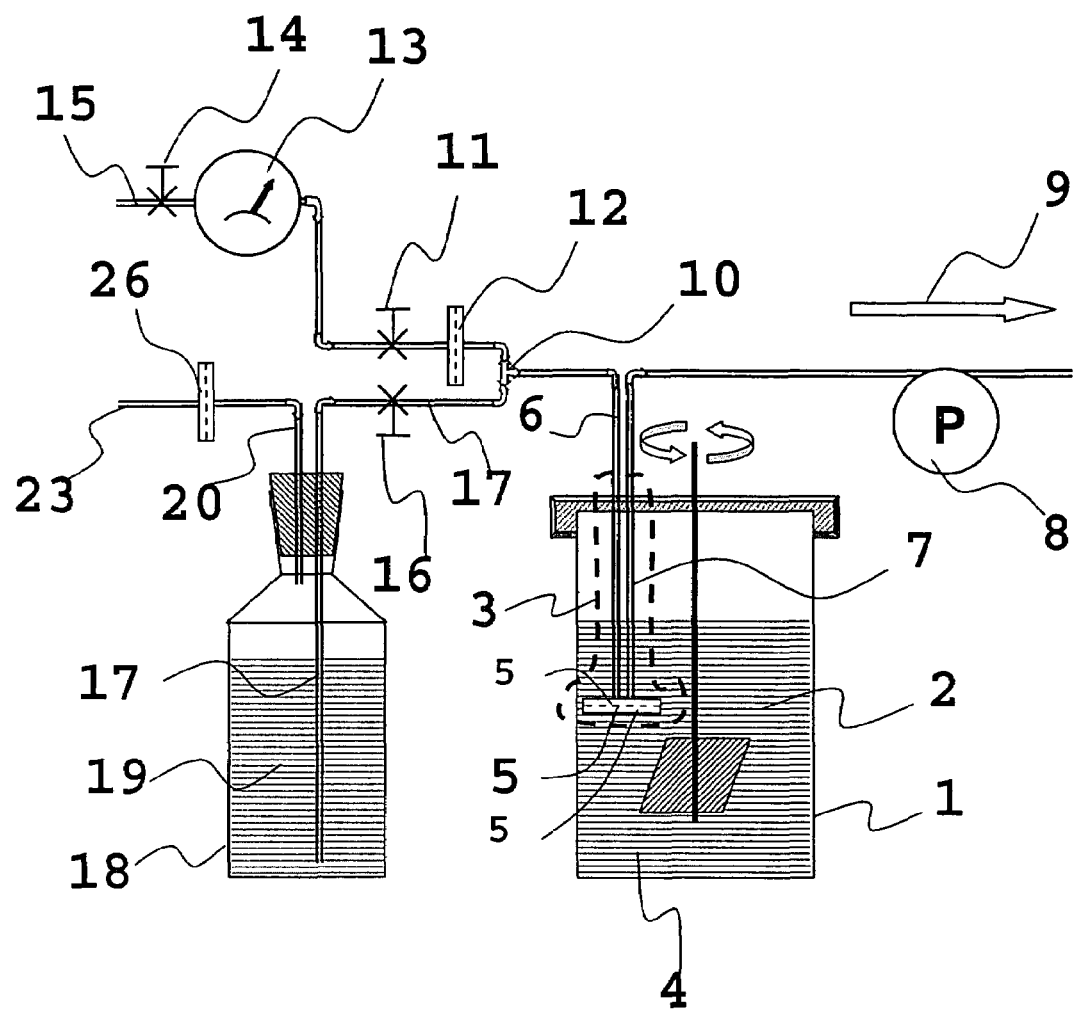

The present application claims priority to German Patent Application No. 102 46 262.3, filed Oct. 2, 2002, which application is incorporated herein fully by this reference.

DESCRIPTION

The invention relates to a device and a method for extracting liquid samples from containers and/or tubes filled with a medium, in particular from fermenters, via a filter membrane by means of a partial vacuum.

A device for extracting liquid samples from a fermenter is known from DE 32 49 399 T1. For the extraction of the sample, the device has a sampler in the form of a normally closed valve whose body has a circular projection on the side in contact with a sample collector, with said projection being designed to accommodate a circular groove in the housing of a normally closed valve in the sample collector. Arranged between the sample collector's normally closed valve and a stop on the sample collector there is a bacteriological filter at a distance from the sample collector's normally closed valve. Due to this distance, when a sample is extracted, the intermediate space within the device is also necessarily filled with the sample liquid, but this is not collected in the sample collector as a liquid sample for investigation. The resulting dead volume of the sample extracted has the effect that, on the one hand, the sampling cannot be performed economically in relation to the required sample volume per sampling and, on the other, a residual volume of the previous sample remains in the device, which, due to its non-sterile properties, can result in the falsification of the test results on the subsequent sampling with the desired sterility.

Also known are commercially available sampling devices for extracting samples from fermentation performed in a bioreactor with a volume of 5 liters, for example, which have a bar-shaped device and a three-way value at their outlet, such as that disclosed, for example, in U.S. Pat. No. 5,948,998. The three-way valve is used to divert the flow during the extraction of the sample from the route between the sampling probe and the outlet to a route between an overflow and the outlet. A diversion of the flow routes of this kind takes place when a sample of the desired volume has been sent to a pipe system downstream of the sample probe.

This diversion process separates off the liquid flow within the device thus achieving intensified intermixing of the sample flow. In this case, the more intensive intermixing results in an increase in the required sample volume or the number of samples to be extracted until a constant substance concentration is established within the sample, since back-mixing of individual substances takes place due to the non-ideal expulsion from the device of the liquid sample from the previous sampling performed. Since sampling devices of this kind have a dead volume, the remaining sample liquid cannot be fully expelled from the device and therefore back-mixing takes place due to the fluid dynamics of the sample liquid.

Back-mixing also takes place due to the different diffusion coefficients of the constituent substances in the sample.

DE 196 30 886 C1 relates to a sample device which permits fluidic diodes for dropwise metering of the sample to be extracted and a calibration solution. The fluidic diodes are arranged between the filter membrane facing the medium and a sensor for the detection of specific test data. Since the actual fluidic diodes have small dimensions, the dead space between the filter membrane and the sensor is minimised.

Sampling devices of this kind also have a dead volume within the dead space during the sampling, which, on the one hand, necessitate a higher volume of sampling and, on the other, give rise to the risk of the residual sample from the previous sampling present in the dead volume being mixed with the sample substances for the new sampling.

With the aforementioned devices, the integrity of the filter membrane can only be checked to a limited extent or with a large amount effort, for example involving the removal of the filter membrane. Any leaks in the filter membrane cause the sterile boundary of the container or the tubing to be disrupted and the medium to be made non-sterile.

In addition, the tightness of the filter membrane can only be checked before the installation and after the removal of a sampling device so that it is always necessary to wait for the end of the entire process or measuring cycle before an integrity test of this kind can be performed.

Consequently, it was the object of the present invention to provide a device and a method for extracting liquid samples from containers and/or tubes filled with a medium via a filter membrane, with which it is possible to extract the sample without any dead volume under reliably sterile conditions and which can be checked at any time by means of an integrity test.

The central idea behind the invention is, in a device for extracting liquid samples from containers and/or tubes filled with a medium. in particular from fermenters, via a filter membrane by means of a partial vacuum, which may be generated, for example, by a pump, to manufacture the filter membrane arranged within a sample probe from a material acting as a sterile boundary, whereby a supply line which can be used to guide gas and a discharge line which can be used to guide the sample are arranged on the sterile boundary side of the filter membrane. The discharge line which can be used to guide the sample is connected to the pump for the creation of a partial vacuum causing the sample to be drawn out of the medium through the filter membrane.

Following the extraction of a sample with a predetermined sample volume, which is regulated, for example, by means of the pump, the sample is drawn off with an additional slight gas overpressure, which is supplied to a rear side of the filter membrane facing the device by means of the supply line, through the discharge line out of the sampling device's pipe system. At the same time, the pipe system is reliably emptied by means of the gas supplied. This ensures there is no dead space within the sampling device in which a dead volume can form. This means it is possible to extract the sample in the desired sample volume for testing even with small volume quantities without any requirement for an additional sample volume for the provision of a dead volume.

Since the filter membrane is equipped with the material acting as a sterile boundary, the extraction of a sterile sample is guaranteed on condition that the pipe system and the remaining parts of the sampling device are sterile per se.

Even if the membrane has a leak, the sterile function of the sampling device is guaranteed provided that the pressure drop in the pipe system caused by the leak is continuously compensated during the sample process by the gas to be supplied. Although the defective filter membrane may result in some rinsing liquid for the optional rinsing out of the pipe system entering the medium, the dilution of the medium by the rinsing liquid, which could be distilled water, for example, does not have any identifiable influence on the concentration of the substances contained in the medium.

The gas used to empty the pipe system is, for example, compressed air, which acts like a hydrophobic medium. The filter membrane, on the other hand, is made of a hydrophilic material which can only be penetrated when there is a high gas overpressure. The reliable emptying of the pipe system caused by these properties of the gas and the filter membrane material without the filter membrane being penetrated in the direction of the medium means that not only the pipe system, but also the remaining parts of the device are completely freed of the sample liquid from the previous sampling. Hence, the complete emptying of the interior of the device of sample liquid and the resulting dead-volume-free sampling is achieved in a simple way.

Advantageously, it is also possible to take a sterile-filtered sample from non-sterile media, since the filter membrane acts as a sterile boundary. Sterile-filtered samples of this kind are usually characterised by longer storage lives.

Since automatic emptying takes place in a simple and effective way following the sampling, the sampling device according to the invention may be used as an automated sampling module and permits the connection of detection systems that are used for in-process monitoring and the regulation/control of the sample extracted and the device according to the invention.

In addition, by means a suitable combination of the sample volume to be extracted, the delivery rate set by the pump and the required time for the emptying of the pipe system, the time required for a sampling process can be kept sufficiently short for online measurements.

An integrity test for checking the tightness of the filter membrane is possible at any time. A test of this kind can be performed before and after a sampling process and consequently makes it possible to increase the operational reliability of the container, which can be a bioreactor, in conjunction with the sampling device attached thereto and improve the handling of the sampling device.

For an integrity test to test the function of the sampling device in situ, the supply line which can be used to guide gas is coupled to a first gas-bearing connecting line for connecting the supply line to a gas supply connection. A coupling of this kind is also required to supply the gas for emptying the pipe system.

A first and second valve are arranged in the area of a first and a second end of the first gas-bearing connecting line according to a preferred embodiment so that the connecting line can be closed on both sides by means of the valve. In addition, a pressure sensor is arranged in the gas-bearing connecting line and a first sterile filter in the area of the gas supply connection within the gas-bearing connection line so that the sterile operation of the pipe system and in particular of the gas-bearing connecting line is ensured and it is possible to check the normal slight overpressure within the gas line.

According to one preferred embodiment, the supply and discharge lines are designed so they are suitable for supplying and discharging rinsing liquid to and from the filter membrane. The rinsing liquids are fed into the supply line which can be used to guide gas by means of a second rinsing liquid-bearing connecting line in and are used to rinse the entire pipe system and the filter membrane in order to prevent jamming and clogging, in particular of the discharge line, by the constituents of the sample substances. The rinsing liquid is a sterile liquid. After the rinsing process, pipe system is again emptied with gas from the first connecting line with a slight overpressure. A rinsing process of this kind can be optionally be performed between two sampling processes.

Advantageously, a method for extracting liquid samples from containers and/or tubes filled with the medium by means of the filter membrane comprises the following steps:
the supply of the gas to the filter membrane arranged in the sample probe and comprising a material acting as a sterile boundary on the sterile boundary side of the filter membrane by means of the supply line that may be closed against other lines by at least one valve
the discharge of the gas from the filter membrane by means of the discharge line and a device functioning as a valve, such as a pump, until the supply and discharge lines are free of the sample
the closure of at least one valve to uncouple the supply line from the gas supply connection
the extraction of the required volume of the sample from the medium by means of the discharge line and a partial vacuum, which may also be generated by means of the pump and
the transportation of the sample out of the discharge line by means of new gas supplied by means of overpressure.

In addition, to avoid clogging and jamming of the of the discharge line, the method may include a step involving the supply of rinsing liquid and for the performance of the integrity tests, the supply of gas with the interior of the device being sealed against the surrounding systems by means of valves.

Other advantageous embodiments are described in the subclaims.

Figure 2:
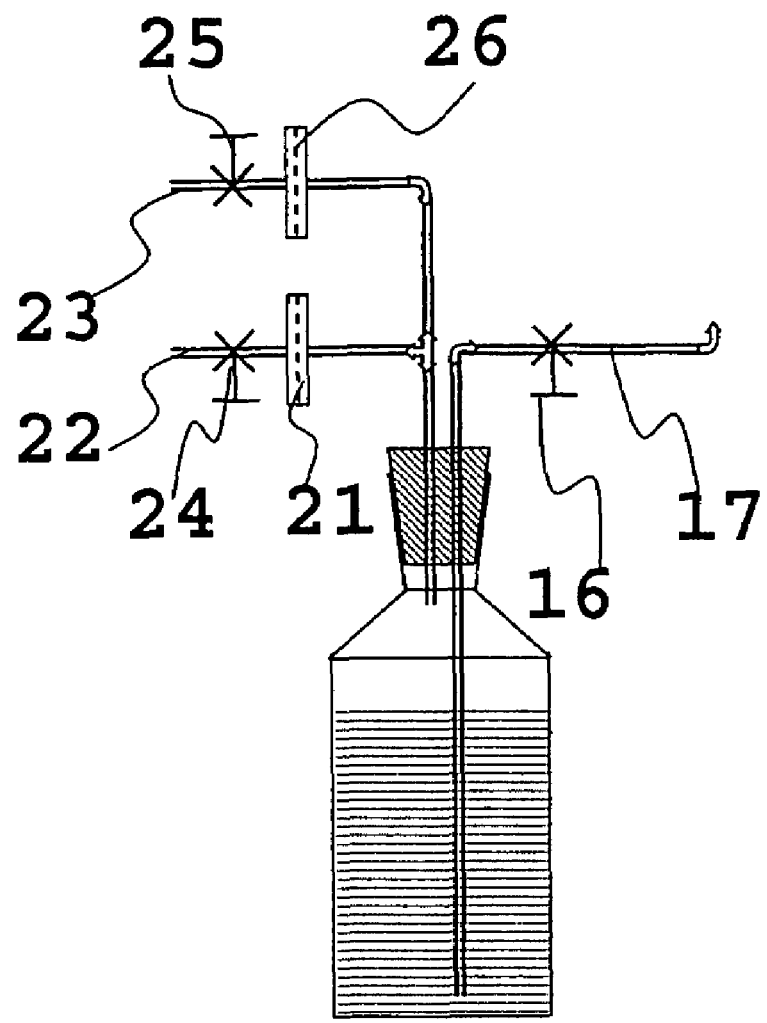
Figure 3:
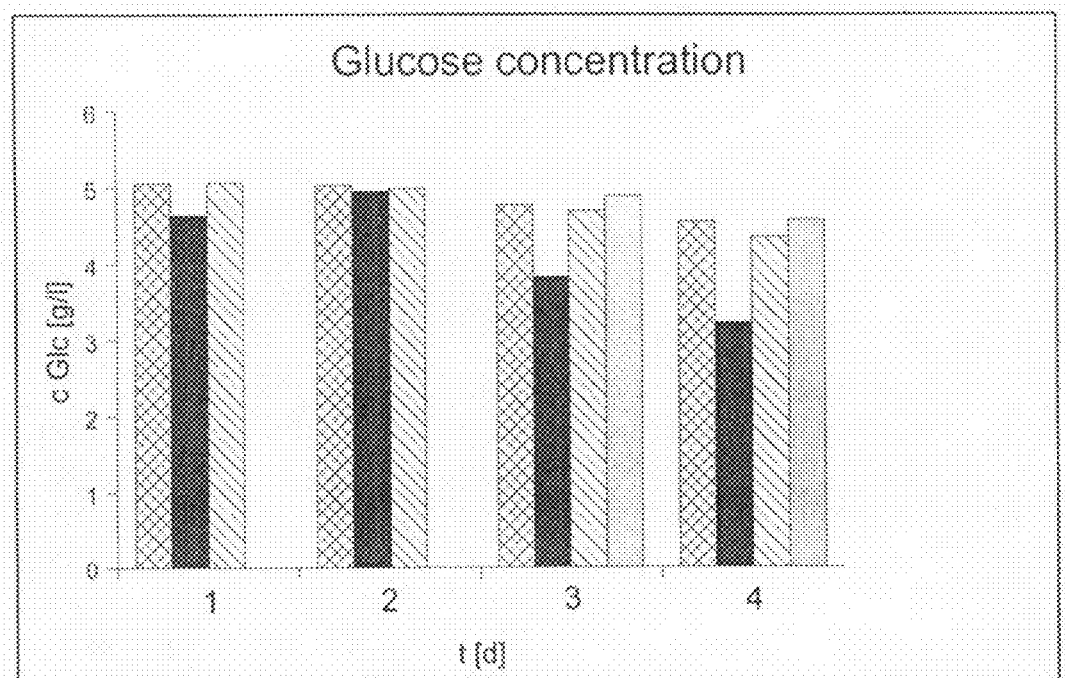
Figure 4:
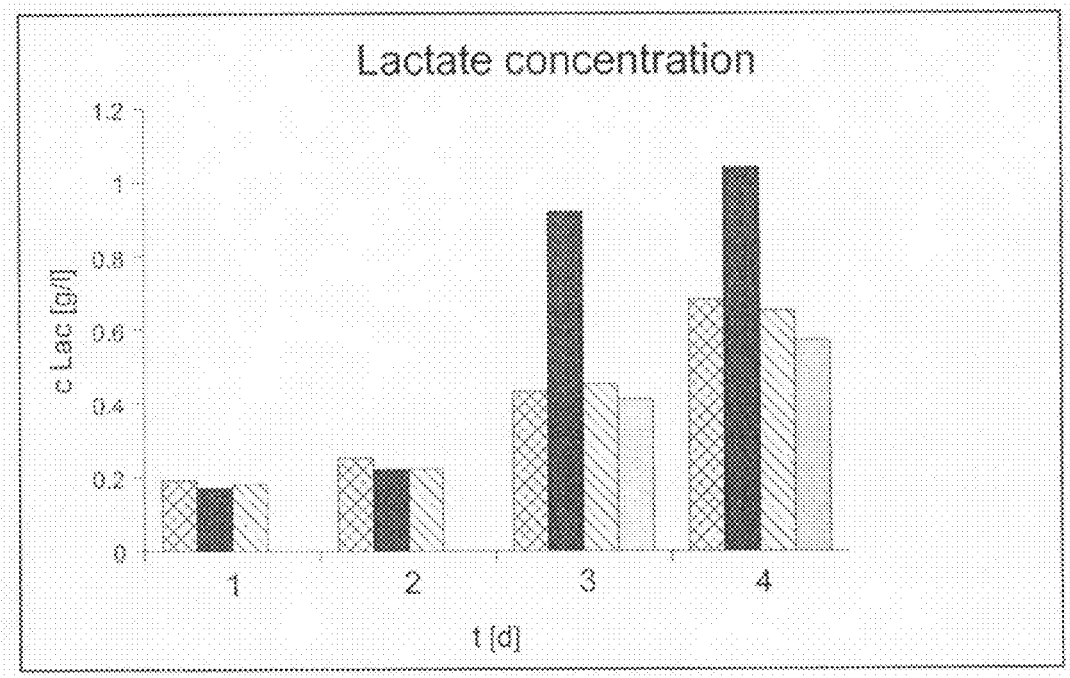

Advantages and expediencies may be determined from the following description in conjunction with the drawings in which:

FIG. 1 shows a schematic representation of a device for extracting samples according to a first embodiment of the invention FIG. 2 shows a schematic representation of a section of the device for extracting samples according to a second embodiment of the invention FIG. 3 depicts measured glucose concentrations over a specific period for sampling processes with a comparative representation of sampling by means of a device according to the invention and by means of a conventional, commercially obtainable device, and FIG. 4 depicts measured lactate concentrations over a specific period during sampling processes with a comparative representation of sampling by means of a device according to the invention and by means of the conventional, commercially obtainable device.

FIG. 1 is a schematic representation of a device for extracting samples from a container filled with a medium according to one embodiment of the invention. Introduced into the medium 2 contained in the container 1 is a sample probe 3 and a stirrer 4 to stir the medium 2. Arranged within the sample probe 3 is a filter membrane comprising a material acting as a sterile boundary. The filter membrane 5 comprises a sterile rear boundary 5a and front boundary 5b facing the medium, whereby the medium may be sterile or non-sterile.

Arranged on the rear boundary 5a of the filter membrane 5, i.e. on the sterile boundary side of the filter membrane, are a supply line 6 which can be used to guide gas and a discharge line 7 which can be used to the guide the sample. The discharge line 7 can be used to drain a sample, which is drawn in by means of a partial vacuum from a pump 8 through the filter membrane 5 from the medium, into a detector device (not shown here) or a storage container (not shown here) as indicated by the arrow 9.

The supply line 6 is connected by means of a T-piece 10 with a first gas-bearing connecting line, which is in turn connected to a gas supply connection 15. The gas supply connection 15 is used to supply compressed air to the supply line 6 if closable valves 11 and 14 are in their open position.

A sterile filter 12 is provided in order to guarantee the supply of sterile compressed air.

In addition, the pressure of the compressed air supplied under slight overpressure is checked by means of a manometer 13.

Connected to the other end of the T-piece 10 is a second rinsing liquid-bearing connecting line 17, which is connected to a container 18, in which rinsing liquid 19, such as, for example, distilled water, is present in a sufficient quantity. A gas and rinsing liquid connecting line 20 connects the container 18 by means of a second sterile filter 26 arranged therein to another gas supply connection 23 to provide pressure compensation for the container 18.

The connection of the gas supply connection 23 is optional.

If a rinsing process is to be performed, a valve 16 to the supply line 8 is opened, while the valves 11 and 14 in the first gas-bearing connecting line are closed. When the rinsing liquid has left the supply and discharge lines 6, 7 via the pump 8 and the lines 6, 7 and the rear boundary 5a of the filter membrane have been rinsed, the valve 16 is closed and the first and second valves 11, 14 are opened in order to effect the drainage of the pipe system with the supply and discharge lines 6, 7 by means of the sterile compressed air supplied.

A sampling process is performed in the following sequence:

While the first and second valves 11, 14 are closed, the pump 8 generates a partial vacuum within the pipe system which transports a sample out of the medium 2 to be analysed through the sterile boundary out of the sample probe. The desired sample volume is regulated by means of the pump strength of the pump 8. When a predetermined sample volume is achieved with a predetermined transport time, the sample is transported with an additional slight compressed air overpressure with a closed valve 16 and open valves 11 and 14 out of the pipe system with the lines 6, 7 and into a storage container (not shown here). At the same time, the compressed air supplied reliably effects the drainage of the pipe system so that it is free of the sample.

To enable the performance of an integrity test to check the function of the sampling device, compressed air is supplied via the gas supply connection 15 with a closed valve 16 and inoperative pump 8 to generate an overpressure in the pipe system. The overpressure is retained after the closure of the valve 14 as long as the filter membrane 5 which forms the sterile boundary is tight. If, on the other hand, the pressure drops, this is an indication that the filter membrane 5 is not tight. This means that the device can be validated by connecting an integrity measuring device.

FIG. 2 is a schematic representation of a section of the device for extracting samples according to a second embodiment of the invention. In this embodiment, additionally, a rinsing liquid supply connection 22 is connected to the container 18 via a rinsing liquid-bearing part of the line 20 and an intermediately arranged additional sterile filter 21 and another valve 24. The rinsing liquid supply connection 22 is used to refill the container 18 with rinsing liquid.

The gas-bearing part of the line 20 also has another valve 25 between the filter 26 and the gas supply connection 23 for the supply, discharge or metering of gas.

FIG. 3 is a diagram showing a comparative representation of a glucose concentration over a certain period in samples taken in sampling processes using a device according to the invention and a commercially available conventional device.

Both sampling devices were installed in a bioreactor. The bioreactor was sterilised and filled with a sterile medium, carriers and cells. The growth of the cells was intended to change the glucose and lactate concentration in the medium.

Following the conclusion of all preparations and sterilisation, a membrane test was performed on the device according to the invention. Then one sample was extracted with each of the devices and the glucose and lactate concentration determined. In the case of the conventional sampling device, a first sample had to be discarded due to the dead volume present. The sample volume to be discarded until a constant concentration of glucose and lactate was obtained was determined. In the conventional device, there was no ideal expulsion of the sample liquid from the pipe system, instead there was a back-mixing of individual substances in the flow contained in the pipe system. The back-mixing was caused by the different diffusion coefficients of the substances in the sample and in addition by the fluid-dynamic properties of the dead volume and sample liquid.

The extraction of the sample by means of the conventional device did not take place continuously. The valve in this conventional device was switched as a three-way valve from a flow route between the sample probe and an outlet to a flow route between an overflow connection and the outlet when a 2 ml sample volume had been transported into the pipe system.

This separated the liquid flow in the interior of the device and the intermixing in the flow was further intensified. In this case, the greater intermixing resulted in the enlargement of the sample volume required until a constant concentration was obtained. For this reason, for the summary, the absolute value of the total volume extracted with the conventional device was reduced to approximately 2.5 ml.

The following results were obtained during the fermentation:

Following sterilisation, water vapour was condensed in the interior of the conventional device filled the device's dead volume. When the pump was switched on, there was a clear difference between the colourless condensate and red-coloured medium. The collected and measured dead volume was approximately 0.6 ml. The medium samples were collected in Eppendorf tips. With the conventional device, it was necessary to collect at least two samples each with a sample volume until a constant measured substance concentration was obtained. This applied to both the glucose concentration and the lactate concentration shown in FIG. 4. This process was repeated on the following days. This resulted in an additional consumption of the medium to be extracted of between 2-4 ml (100-200%) compared to the sampling process by means of the sampling device according to the invention.

The following Table 1 and the diagrams in FIGS. 3 and 4 provide a comparative representation of the extraction of samples from the bioreactor until equalisation of concentration of glucose and lactate was achieved with extraction by means of the device according to the invention and the conventional device in the form of measuring results:

TABLE 1

| t[d] | Invention 1st sample | Prior art 1st sample | Prior art 2nd sample | Prior art 3rd sample |
|---|---|---|---|---|
| Glucose (g/l) | | | | |
| 1 | 5.06 | 4.64 | 5.07 | |
| 2 | 5.03 | 4.95 | 4.99 | |
| 3 | 4.77 | 3.83 | 4.69 | 4.88 |
| 4 | 4.55 | 3.23 | 4.35 | 4.57 |
| Lactate (g/l) | | | | |
| 1 | 0.19 | 0.17 | 0.18 | |
| 2 | 0.25 | 0.22 | 0.22 | |
| 3 | 0.43 | 0.92 | 0.45 | 0.41 |
| 4 | 0.68 | 1.04 | 0.65 | 0.57 |

In another test, samples with a volume of 1.5-2 ml were extracted many times from a spinner flask with a CaSo solution corresponding to a nutrient broth for sterile tests using the device according to the invention and analysed. The device was sterile for a test period of two weeks. The glucose concentration in the medium in the spinner flask remained virtually constant, apart from measuring device fluctuations in the enzyme sensor. These may be attributed to the fact that the enzyme sensor reacted sensitively to, for example, ageing sensor membranes or inadequate automatic calibration. Table 2 below shows the glucose concentration as measured over several days.

TABLE 2

| t[d] | Concentration [g/l Glc] |
|---|---|
| 0 | 1.23 |
| 4 | 1.06 |
| 5 | 0.99 |
| 6 | 0.67 |
| 7 | 0.96 |
| 8 | 1.05 |
| 9 | 0.98 |
| 11 | 0.98 |
| 12 | 1.00 |

A preliminary test was used to check whether the concentration of glucose in a CaSo solution decreases of its own accord over time. To do this a CaSo solution was incubated in sterile conditions 37° C. An analysis of the CaSo solution found it to be stable over the test period of four weeks as demonstrated in the Table 3 below.

TABLE 3

| t[d] | Concentration [g/l Glc] |
|---|---|
| 0 | 1.52 |
| 19 | 1.52 |
| 21 | 1.51 |
| 27 | 1.52 |

The execution of the invention is not restricted solely to the example described and emphasised aspects but is similarly possible within the scope of the claims in a plurality of modifications which are within the scope of expert capability.

List of reference numbers

| 1 | Container |
|---|---|
| 2 | Medium |
| 3 | Sample probe |
| 4 | Stirrer |
| 5 | Filter membrane |
| 5a | Rear side of the filter membrane |
| 5b | Front side of the filter membrane |
| 6 | Supply line |
| 7 | Discharge line |
| 8 | Pump |
| 9 | Discharge direction |
| 10 | T-piece |
| 11, 14, 16, 24, 25 | Valves |
| 12, 21, 28 | Sterile filter |
| 13 | Manometer |
| 15, 23 | Gas supply connection |
| 17 | Rinsing-liquid bearing connecting line |
| 18 | Container |
| 19 | Rinsing liquid |
| 20 | Gas and rinsing liquid connection line |
| 22 | Rinsing liquid supply connection |
| 23 | Gas supply connection |

The invention claimed is:

1. Device for extracting liquid samples from containers and/or tubes filled with a medium via a filter membrane by means of a partial vacuum, characterised in that the filter membrane arranged within a sample probe comprises a material acting as a sterile boundary, whereby a supply line which can be used to guide gas and a discharge line which can be used to guide the sample are arranged on the sterile boundary side of the filter membrane wherein the supply and discharge lines are designed to be suitable to supply and discharge rinsing liquids to and from the filter membrane and the supply line is connected to a second rinsing liquid-bearing connecting line which is connected to a second container containing a rinsing liquid, wherein the second container is connected to a rinsing liquid supply connection via a gas and rinsing liquid connecting line with an another sterile filter arranged therein.

2. Device according to claim 1, characterised in that the material acting as a sterile boundary is hydrophilic.

3. Device according to claim 1, characterised in that the supply line which can be used to guide gas contains a hydrophobic gas.

4. Device according to claim 1, characterised in that the supply line which can be used to guide gas and the discharge line are designed to be suitable to supply and discharge gas with overpressure to and from the filter membrane.

5. Device according to claim 1, characterised in that the supply line which is able to guide gas is connected to a first gas-bearing connecting line to connect the supply line to a gas supply connection.

6. Device according to claim 5, characterised in that a first and second valve are arranged in the area of the first and second end of the connecting line.

7. Device according to claim 5, characterised in that a pressure sensor is arranged in the gas-bearing connecting line.

8. Device according to claim 5, characterised in that a first sterile filter is arranged in the gas-bearing connecting line.

9. Device for extracting liquid samples from containers and/or tubes filled with a medium via a filter membrane by means of a partial vacuum, characterised in that the filter membrane arranged within a sample probe comprises a material acting as a sterile boundary, whereby a supply line which can be used to guide gas and a discharge line which can be used to guide the sample are arranged on the sterile boundary side of the filter membrane wherein the supply and discharge lines are designed to be suitable to supply and discharge rinsing liquids to and from the filter membrane and the supply line is connected to a second rinsing liquid-bearing connecting line which is connected to a second container containing a rinsing liquid, wherein the second container is connected to another gas supply connection via a gas and rinsing liquid connecting line with another sterile filter arranged therein.

10. Device according to claim 9, characterised in that the discharge line is connected to a device acting as a valve.

11. Device according to claim 9, characterised in that the material acting as a sterile boundary is hydrophilic.

12. Device according to claim 9, characterised in that the supply line which can be used to guide gas contains a hydrophobic gas.

13. Device according to claim 9, characterised in that the supply line which can be used to guide gas and the discharge line are designed to be suitable to supply and discharge gas with overpressure to and from the filter membrane.

14. Device according to claim 9, characterised in that the supply line which is able to guide gas is connected to a first gas-bearing connecting line to connect the supply line to a gas supply connection.

15. Device according to claim 14, characterised in that a first and second valve are arranged in the area of the first and second end of the connecting line.

16. Device according to claim 14, characterised in that a pressure sensor is arranged in the gas-bearing connecting line.

17. Device according to claim 14, characterised in that a first sterile filter is arranged in the gas-bearing connecting line.

18. Method for extracting liquid samples from containers and/or tubes filled with a medium via a filter membrane by means of a partial vacuum comprising the following steps:
   supplying a gas to the filter membrane arranged in the same probe and comprising a material acting as a sterile boundary on the sterile boundary side of the filter membrane by means of a supply line which may be closed against other lines by at least one valve;
   discharging the gas from the filter membrane by means of the discharge line and opening of a device arranged in the discharge line functioning as a valve until the supply and discharge lines are sample-free;
   closing at least one valve to uncouple the supply line from the gas supply connection;
   extracting the required volume of the sample from the medium by means of the discharge line and a partial vacuum present in the discharge line;
   transporting the sample out of the discharge line by means of new gas supplied by means of overpressure.

19. Method according to claim 18, characterised in that to avoid clogging and jamming within the discharge line caused by the constituents of the sample, after the step in which the sample is transported out of the discharge line, a rinsing liquid is supplied via the supply line and discharged via the discharge line.

20. Method according to claim 19, characterised in that, after the step in which the rinsing liquid is supplied and discharged, the steps in which the gas is supplied and discharged are repeated.

21. Method according to claim 18, characterised in that an integrity test for checking/validating the sampling function comprises the following steps:
   closing the discharge line by a device acting as a valve;
   supplying gas to the supply and discharge lines to generate a defined overpressure;
   closing another valve to uncouple the gas supply connection from the supply line with the involvement of a pressure sensor;
   observing any possible gas and/or liquids entering/or leaving the pipe system; and
   observing the pressure stability by means of the pressure sensor as an indicator of the integrity of the filter membrane.

* * * * *

UNITED STATES PATENT AND TRADEMARK OFFICE
CERTIFICATE OF CORRECTION

PATENT NO. : 7,343,925 B2  
APPLICATION NO. : 10/530156  
DATED : March 18, 2008  
INVENTOR(S) : Heiner Sann, Andreas Bock and Udo Reichl It is certified that error appears in the above-identified patent and that said Letters Patent is hereby corrected as shown below:

On the Title Page, Item (73)

Please change "Max-Planck Gesellschaft Zur" to --Max-Planck-Gesellschaft zur Forderung der Wissenschaften e.v.--

Signed and Sealed this

Twenty-ninth Day of July, 2008

JON W. DUDAS  
*Director of the United States Patent and Trademark Office*